United States Patent
Kim

(10) Patent No.: US 8,672,677 B1
(45) Date of Patent: Mar. 18, 2014

(54) DENTAL TRAY

(71) Applicant: Jason J. Kim, Manhasset, NY (US)

(72) Inventor: Jason J. Kim, Manhasset, NY (US)

( * ) Notice: Subject to any disclaimer, the term of this patent is extended or adjusted under 35 U.S.C. 154(b) by 0 days.

(21) Appl. No.: 13/788,723

(22) Filed: Mar. 7, 2013

(51) Int. Cl.
*A61C 9/00* (2006.01)

(52) U.S. Cl.
USPC .......................................................... 433/43

(58) Field of Classification Search
USPC ...................... 433/37, 43, 41, 42, 44, 45, 214
See application file for complete search history.

(56) References Cited

U.S. PATENT DOCUMENTS

| | | | |
|---|---|---|---|
| 305,900 A * | 9/1884 | Crowther | 433/43 |
| 880,328 A | 2/1908 | Sadler | |
| 1,464,987 A | 8/1923 | Haggard et al. | |
| 1,486,039 A * | 3/1924 | Santos | 433/43 |
| 1,493,417 A | 5/1924 | Arnett | |
| 1,608,632 A | 11/1926 | Strusser | |
| 1,634,717 A | 7/1927 | Light | |
| 2,549,184 A | 4/1951 | Eliot | |
| 4,227,877 A | 10/1980 | Tureaud | |
| 4,375,965 A | 3/1983 | Weissman | |
| 4,484,890 A | 11/1984 | Jouvin | |
| 4,530,662 A | 7/1985 | Andersson | |
| 4,689,010 A | 8/1987 | Wolfe | |
| 4,907,966 A | 3/1990 | Kesling | |
| 5,316,474 A | 5/1994 | Robertson | |
| 5,336,086 A | 8/1994 | Simmen | |
| 5,513,985 A | 5/1996 | Robertson | |
| 5,772,432 A | 6/1998 | Jordan | |
| 6,079,977 A * | 6/2000 | Persichetti | 433/37 |
| 6,213,768 B1 | 4/2001 | Wright | |
| 6,302,690 B1 | 10/2001 | Brandhorst et al. | |
| 6,428,315 B1 | 8/2002 | Prestipino | |
| 6,457,973 B1 | 10/2002 | Fetz et al. | |
| 6,629,841 B1 | 10/2003 | Skinner | |
| 6,749,428 B2 | 6/2004 | DiMarino et al. | |
| 6,875,016 B2 | 4/2005 | Burgio et al. | |
| 7,021,929 B2 | 4/2006 | DiMarino et al. | |
| 7,125,251 B2 | 10/2006 | Livolsi | |
| 7,273,371 B2 | 9/2007 | Massad | |
| 2007/0148612 A1 | 6/2007 | Massad | |
| 2008/0096158 A1 | 4/2008 | Dorfman | |
| 2008/0311536 A1 | 12/2008 | Kim et al. | |

OTHER PUBLICATIONS http://solutions.3m.com.au/wps/portal/3M/en_AU/3M-ESPE-APAC/dental-professionals/products/category/impression/directed-flow-impression-tray/ (copyright notice date 2013).
http://www.premusa.com/dental/prosthetic.asp (copyright notice date 2000-2004).
http://practicon.com/product.aspx?id=39500 (copyright notice date 2013).
http://www.borderlock.com/disposable.htm (copyright notice date 2012).

* cited by examiner

*Primary Examiner* — Heidi M Eide
(74) *Attorney, Agent, or Firm* — Greenberg Traurig, LLP

(57) ABSTRACT

A dental tray for use in taking an impression of a person's teeth is provided. More particularly, the dental tray includes a first section having a longitudinal axis and a second section sized and shaped so as to be mounted at least partially within the first section. The first and second sections are sized and shaped so as to define a trough therebetween for receiving an impression-taking material. The second section is adapted to move relative to the first section in a first direction substantially parallel to the longitudinal axis of the first section. The second section has at least one member movable in a second direction substantially perpendicular to the first direction in response to the movement of the second section in the first direction.

20 Claims, 4 Drawing Sheets

US 8,672,677 B1

DENTAL TRAY

FIELD OF THE INVENTION

The present invention relates to a dental tray for use in taking an impression of a person's teeth.

BACKGROUND OF THE INVENTION

Various dental trays have been developed in the past. For instance, U.S. Pat. Nos. 880,328, 1,464,987, 1,493,417, 1,608,632, 1,634,717, 2,549,184, 4,227,877, 4,375,965, 4,484,890, 4,530,662, 4,689,010, 4,907,966, 5,336,086, 5,772,432, 6,079,977, 6,213,768 6,302,690, 6,428,315, 6,457,973, 6,629,841, 6,749,428, 7,125,251 and 7,273,371 and U.S. Patent Publication No. 2008/0311536 each disclose a device for taking an impression of a patient's teeth. The present invention relates to a dental tray useful in taking an accurate dental impression.

SUMMARY OF THE INVENTION

In accordance with an embodiment of the present invention, a dental tray for use in taking an impression of a person's teeth is provided. More particularly, the dental tray includes a first section having a longitudinal axis and a second section sized and shaped so as to be mounted at least partially within the first section. The first and second sections are sized and shaped so as to define a trough therebetween for receiving an impression-taking material. The second section is adapted to move relative to the first section in a first direction substantially parallel to the longitudinal axis of the first section. The second section has at least one member movable in a second direction substantially perpendicular to the longitudinal axis in response to the movement of the second section in the first direction.

Another embodiment of the present invention involves providing a dental tray for use in taking an impression of a person's teeth. More particularly, the tray includes a first section having a longitudinal axis and first and second ends spaced apart from one another in a first direction substantially parallel to the longitudinal axis of the first section. The tray also includes second section sized and shaped so as to be mounted at least partially within the first section. The first and second sections are sized and shaped so as to define a trough therebetween for receiving an impression-taking material therein. The second section is adapted for movement relative to the first section in the first direction and has first and second movable members, each of which is movable in a second direction substantially perpendicular to the longitudinal axis in response to the movement of the second section in the first direction.

In accordance with yet another embodiment of the present invention, a method for taking an impression of a person's teeth with the use of a dental tray is provided. More particularly, the dental tray includes a first section and a second section. The second section is mounted at least partially within the first section so as to define a trough therebetween and is movable relative to the first section in a first direction which is substantially parallel to a longitudinal axis of the first section. The second section has at least one member movable in a second direction substantially perpendicular to the longitudinal axis in response to the movement of the second section in the first direction. The method includes the steps of placing an impression-taking material in the trough of the tray and inserting the tray into a mouth of the person. The method also includes the steps of moving the tray such that the teeth are inserted into the impression material placed in the trough and moving the second section in the first direction so as to cause the at least one member to move in the second direction.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE INVENTION

Figure 1:
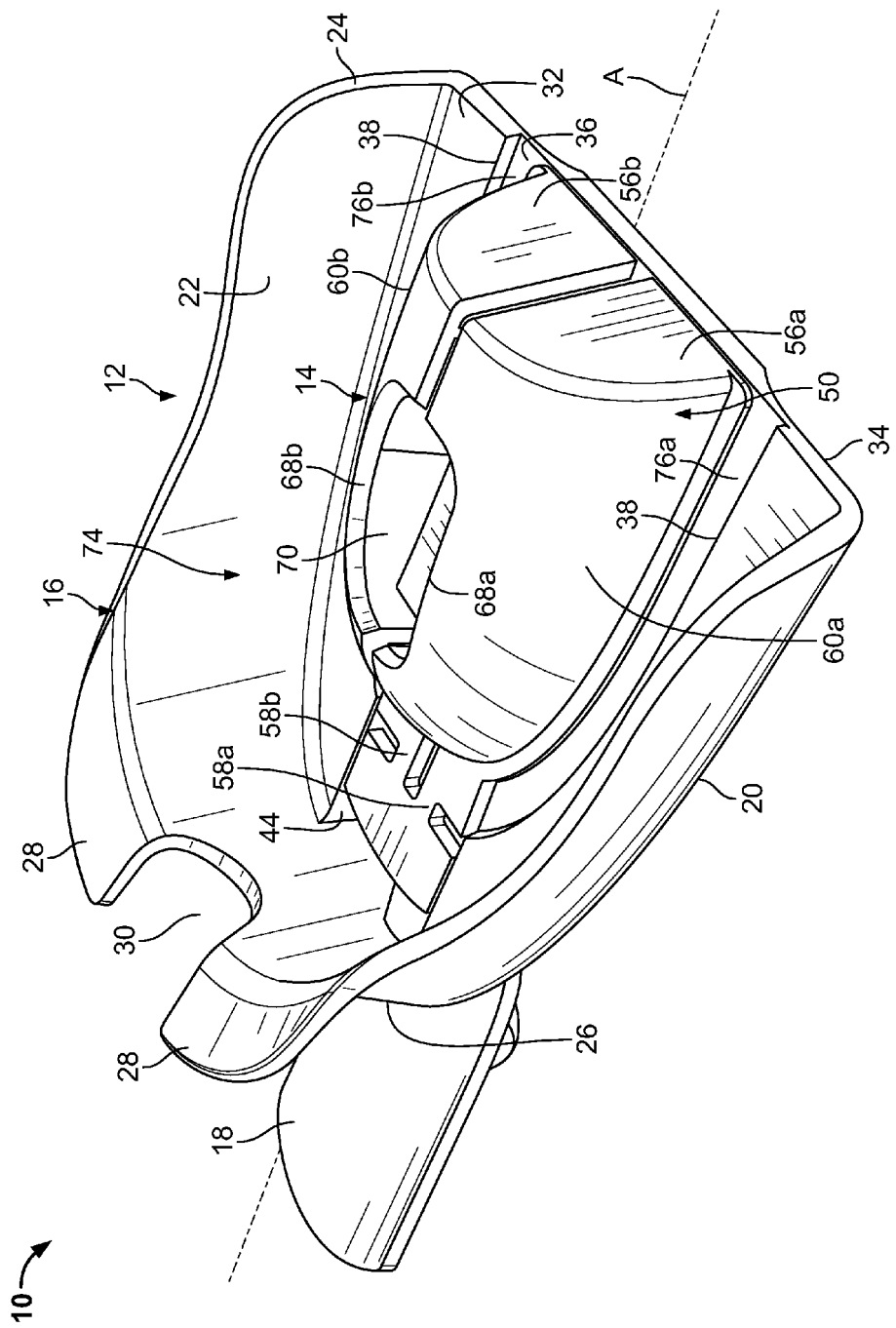
FIG. 1 is a top perspective view of a dental tray constructed in accordance with an embodiment of the present invention.
Figure 2:
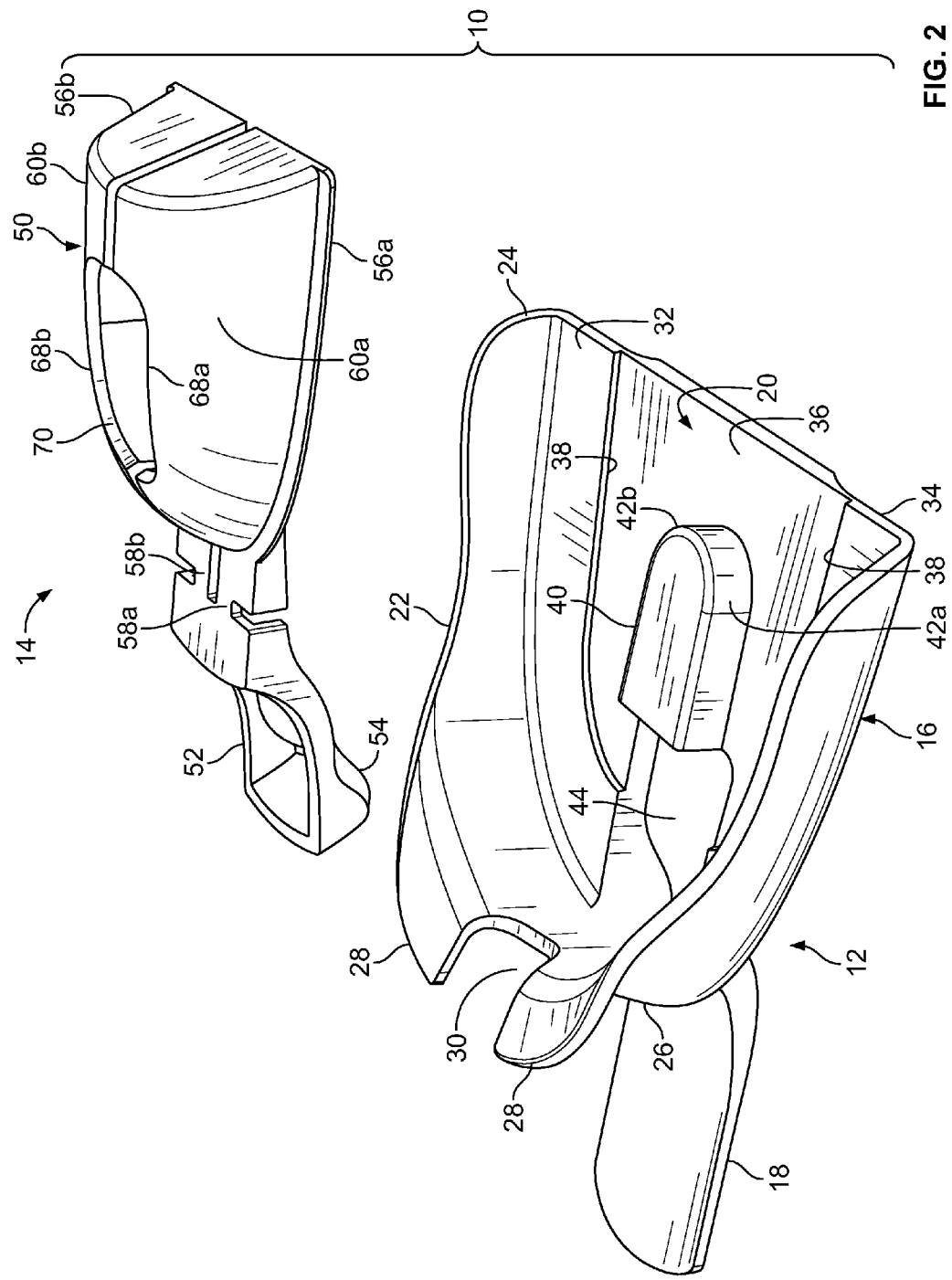
FIG. 2 is an exploded, upper perspective view of the dental tray shown in FIG. 1.

With reference to FIGS. 1 and 2, there is shown a dental tray assembly 10 constructed in accordance with an embodiment of the present invention. More particularly, the dental tray assembly 10, which is adapted for use in taking an impression of upper teeth of a person or a patient, has a longitudinal axis A and includes an outer tray member (i.e., section) 12 and an inner tray member (i.e., section) 14 movably mounted on the outer member 12. The construction of the inner and outer members 12, 14 will be discussed in greater detail below.

Still referring to FIGS. 1 and 2, the outer member 12 includes a tray 16 and a handle 18 extending from the tray 16. More particularly, the tray 16 is provided with a base plate 20, which extends generally in a horizontal manner, and a generally U-shaped outer wall 22, which projects generally vertically from the base plate 20. The tray 16 has an open rear end 24 and a front end 26, which is enclosed by the outer wall 22. Lip support members 28 extend from the outer wall 22 at the front end 26 of the tray 16 for supporting a patient's upper lip when the tray assembly 10 is inserted into the patient's mouth. A notch 30 is provided between the lip support members 28 and extends partially into the outer wall 22 at the front end 26.

Figure 3:
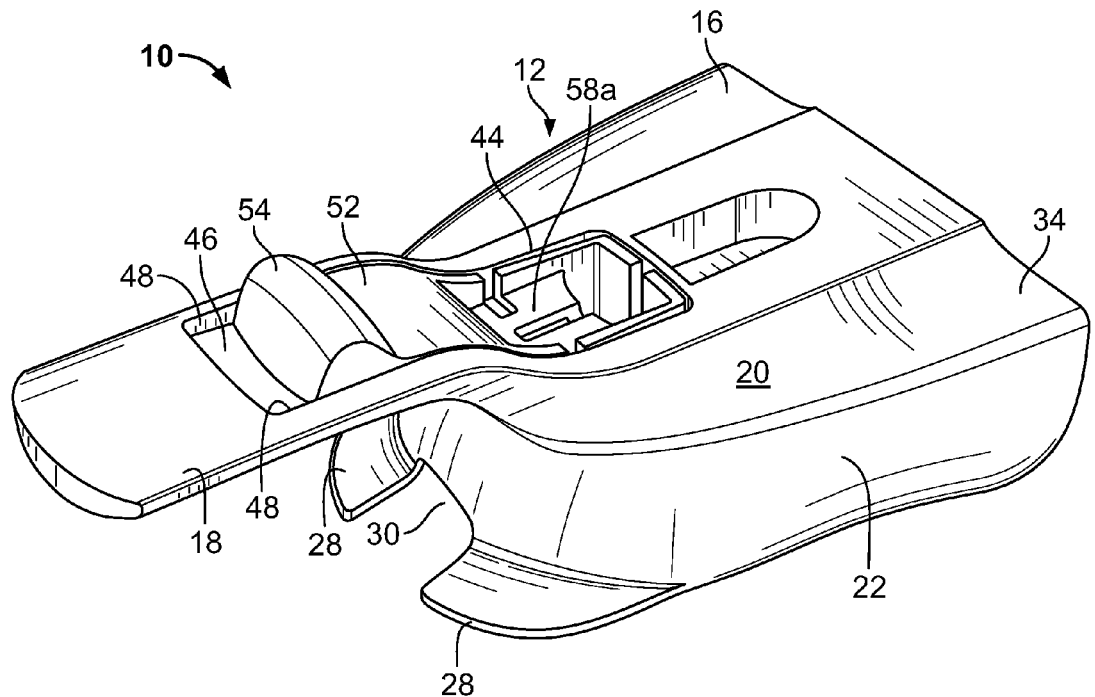
FIG. 3 is a bottom perspective view of the dental tray shown in FIG. 1.

Now referring to FIGS. 1, 2 and 3, the base plate 20 of the tray 16 includes an upper side 32 and a lower side 34. A recessed area 36 is provided generally centrally in the base plate 20. The recessed area 36 has a slightly lower elevation compared to the rest of the upper side 32 of the base plate 20 such that an edge 38 is formed on the upper side 32 defining the recessed area 36. A ramp 40 projects upwardly from the base plate 20 and has a pair of generally curved guide wall portions 42a, 42b on opposite sides thereof. An opening 44 is formed in the base plate 20 adjacent the front end 26 of the tray 16 for purposes to be discussed below. A track 46 is provided in the handle 18 and is defined by a pair of axially extending support walls 48 (see FIG. 3).

Figure 4:
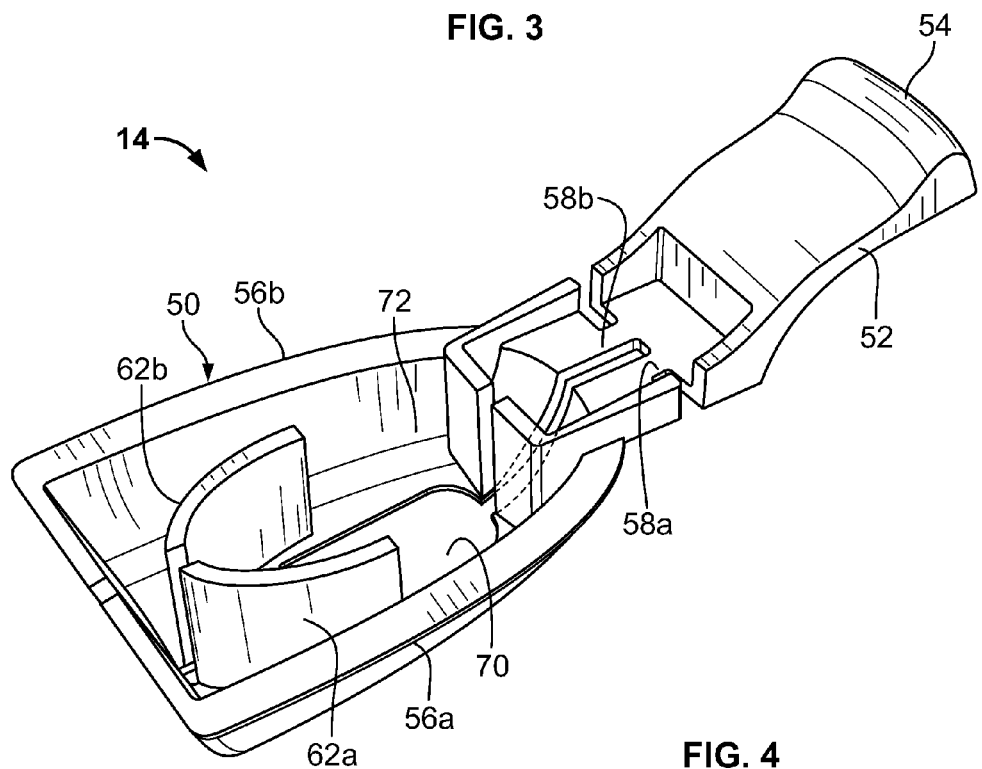
FIG. 4 is a bottom perspective view of an inner member of the dental tray shown in FIG. 1.

With reference to FIGS. 1, 2 and 4, the inner member 14 includes a compression section 50 and a handle 52 extending from the compression section 50 and having a tab 54 at an end thereof. More particularly, the compression section 50 is generally dome-shaped and includes a plurality of compression members 56a, 56b connected to the handle 52 via hinges 58a, 58b (e.g., living hinges), respectively, such that they are laterally pivotable toward or away from each other. More particularly, the compression member 56a is an element that is separate and independent from the compression member 56b. The compression members 56a, 56b have curved, half-dome-shaped walls 60a, 60b, respectively, and curved guides 62a, 62b, respectively. The guides 62a, 62b depend from the walls 60a, 60b, respectively, and are sized and shaped so as to engage the curved wall portions 42a, 42b, respectively, of the outer member 12 (see FIG. 6) for purposes to be discussed hereinbelow.

Figure 5:
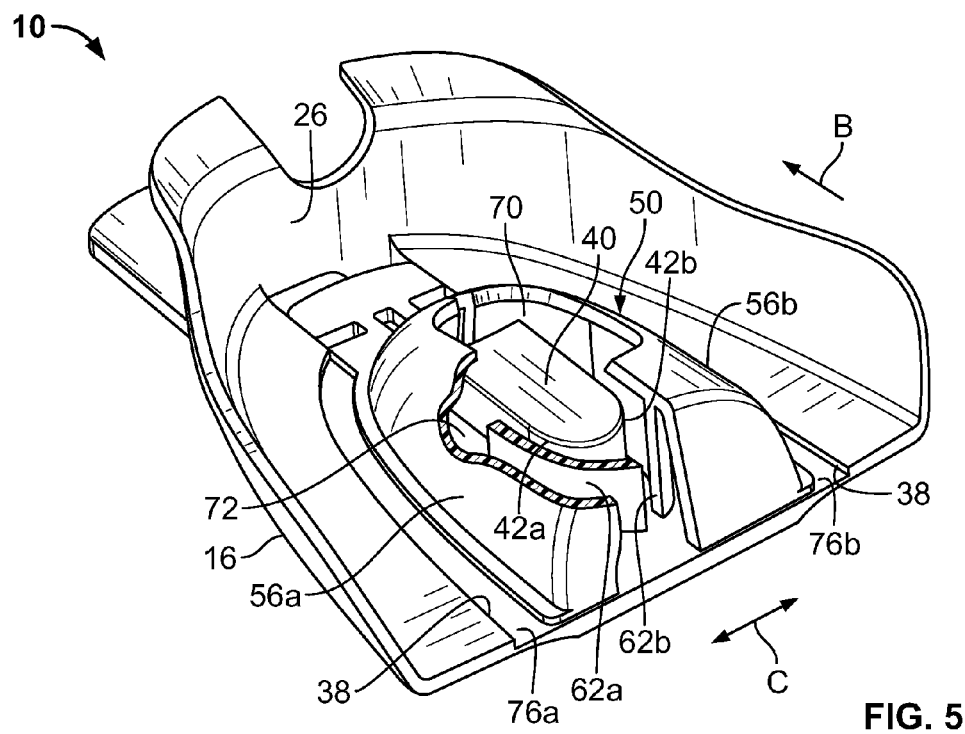
FIGS. 5 and 6 are perspective, partially broken away views of the dental tray shown in FIG. 1, illustrating its operation.

Notches 68a, 68b (see FIGS. 1 and 2) are formed in inner sides of the compression members 56a, 56b, respectively, cooperating to define an opening 70 in the compression section 50. The opening 70 communicates with a cavity 72 (see FIGS. 4 and 5) formed within the compression section 50 for purposes to be discussed hereinbelow.

Now referring to FIGS. 1 and 3, the inner member 14 is assembled with the outer member 12 by inserting the handle 52 of the inner member 14 through the opening 44 in the outer member 12. More particularly, the handle 52 of the inner member 14 is placed in the track 46 formed in the handle 18 of the outer member 12, while the compression section 50 of the inner member 14 is positioned on the recessed area 36 of the outer section 12 such that it covers the ramp 40. In this manner, a generally U-shaped trough 74 is formed between the outer wall 22 of the outer member 12 and the compression section 50 of the inner member 14 for receiving a conventional impression taking material.

Figure 6:
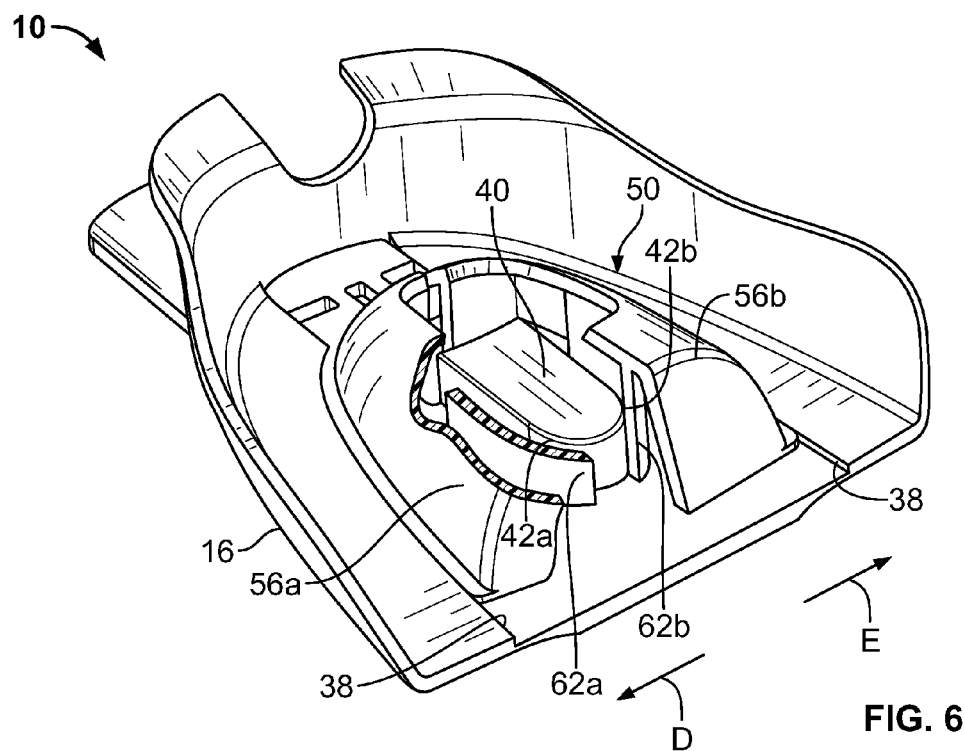

When the compression section 50 is properly assembly with the tray 16 (see FIG. 1), the compression section 50 is movable relative to the tray 16 in an axial direction generally parallel to the longitudinal axis A (as indicated by arrow B in FIG. 5) between its rest position (see FIG. 5) and its retracted position (see FIG. 6). More particularly, in the rest position of the compression section 50, the compression members 56a, 56b are in their respective retracted positions such that they are placed in an abutting fashion with respect to one another (see FIG. 5). In the retracted position of the compression section 50, the compression members 56a, 56b move to their respective expanded positions, in which they are positioned away from each other in a lateral direction (as indicated by arrow C in FIG. 5). When the compression section 50 is in its rest position, spaces 76a, 76b (see FIGS. 1 and 5) are formed between the compression member 56a and the edge 38 and between the compression member 56b and the edge 38, respectively, so as to allow the compression members 56a, 56b to move from their respective retracted positions to their respective expanded positions.

In use, an impression material (not shown) is placed in the U-shaped trough 74 formed between the tray 16 and compression section 50. The compression material can be any conventional compression material. With the handle 18 gripped by a user (e.g., a dentist), the tray 16 and the compression section 50, as assembled, are inserted into the patient's mouth. Thereafter, the tray 16 is moved upwardly toward the pallet of the patient, causing the teeth of the patient to be pressed into the impression material in the trough 74. As the teeth are pressed into the impression material, an excess amount of the impression material flow out of the trough 74. The cavity 72 is adapted to receive an overflow of the impression material through the opening 70 of the compression section 50.

Once the tray assembly 10 is properly positioned in relation to the teeth, the tab 54 of the handle 58 of the inner member 14 is pulled forward in the axial direction (as indicated by arrow B in FIG. 5) such that the compression section 50 moves axially toward the front end 26 of the tray 16 (i.e., to its retracted position). As the compression section 50 moves in the forward axial direction, the guides 62a, 62b of the compression section 50 engage the curved wall portions 42a, 42b, respectively, of the ramp 40, causing the compression members 56a, 56b to move in the lateral direction away from each other (i.e., to their respective expanded positions), as indicated by arrows D and E, respectively, in FIG. 6. As the compression members 56a, 56b expand laterally, they press against the impression material so as to ensure that the impression material is properly applied against the teeth of the patient. In this regard, the edge 38 of the tray 16 is adapted to engage the compression members 56a, 56b so as to inhibit or prevent them from expanding beyond a predetermined extent (see FIG. 6). With the compression members 56a, 56b positioned in their expanded positions, the dental tray assembly 10 is held in place until the impression material cures. Thereafter, the tray assembly 10 is removed from the patient's mouth, and the impression material is removed from the tray assembly 10.

It should be appreciated that the tray assembly 10 of the present invention provides a number of advantages over the prior art discussed above. For instance, the compression members 56a, 56b are adapted to apply additional pressure against an impression material such that the impression material is properly pressed against teeth. As a result, an accurate impression of the teeth can be taken with the use of the tray assembly 10. Moreover, because the handle 52 of the inner tray member 14 is provided in the track 46 of the outer tray member 12, the axial movement of the compression section 50 can be effected with the use of one hand (e.g., with the handle 18 gripped by a person's hand, the tab 54 can be pulled with the index finger of that hand).

It should also be noted that the present invention can have numerous modifications and variations. For instance, while the tray assembly 10 discussed above is adapted for use in taking an impression of upper teeth, it can be modified for use in conjunction with lower teeth. Moreover, the compression section 50 can be modified to have a different shape.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined in the appended claims.

What is claimed is:

1. A dental tray for use in taking an impression of a person's teeth, comprising a first section having a longitudinal axis and a generally U-shaped outer wall; and a second section having a dome-shaped inner member sized and shaped so as to be mounted at least partially within said U-shaped wall of said first section, said U-shaped wall and said dome-shaped member being sized and shaped so as to define a trough therebetween for receiving an impression-taking material, said second section being movable relative to said first section in a first direction which is substantially parallel to said longitudinal axis of said first section, said dome-shaped member having first and second movable members movably attached to said second section, each of said first and second movable members being movable in a second direction substantially perpendicular to said longitudinal axis in response to the movement of said second section in said first direction.

2. The dental tray of claim 1, wherein said first section has a first lateral side and a second lateral side opposite said first lateral side; and said first and second movable members are movable in said second direction toward said first and second lateral sides, respectively, of said first section in response to the movement of said second section in said first direction.

3. The dental tray of claim 2, wherein said first section includes a ramp; and wherein said first and second movable members of said second section are sized and shaped so as to engage said ramp in response to the movement of said second section in said first direction so as to cause said first and second movable members to move in said second direction toward said first and second lateral sides, respectively, of said first section.

4. The dental tray of claim 3, wherein said ramp includes a first wall portion, which is located adjacent said first lateral side of said first section, and a second wall portion, which is located adjacent said second lateral side of said first section; and wherein said first and second movable members have first and second guides, respectively, depending therefrom, said first and second guides being configured to engage said first and second wall portions, respectively, in response to the movement of said second section in said first direction so as to cause said first and second movable members to move in said second direction toward said first and second lateral sides, respectively, of said first section.

5. The dental tray of claim 4, wherein said first and second movable members are positioned adjacent to each other such that they cooperate to define a substantially hollow space in said dome-shaped section, said ramp being positioned in said space.

6. The dental tray of claim 5, wherein each of said first and second movable members has a cutout adjacent a top portion thereof such that an overflow of the impression material can be received in said space from said trough through said cutouts.

7. The dental tray of claim 5, wherein said U-shaped wall and said first and second movable members form said trough therebetween.

8. The dental tray of claim 7, wherein said U-shaped wall has at least one lip support projecting outwardly therefrom.

9. The dental tray of claim 8, wherein said at least one lip support includes a pair of lip supports projecting outwardly from a front end of the U-shaped wall.

10. The dental tray of claim 4, wherein said first section has a first handle portion; and said second section has a second handle portion for moving said second section in said first direction, said first handle portion being substantially aligned with said second handle portion.

11. The dental tray of claim 10, wherein said second section has first and second hinges connecting said first and second movable members, respectively, to said handle portion of said second section.

12. A dental tray for use in taking an impression of a person's teeth, comprising a first section having a longitudinal axis and a generally U-shaped outer wall, said first section including first and second ends spaced apart from one another in a first direction substantially parallel to said longitudinal axis of said first section; and a second section having a dome-shaped inner member sized and shaped so as to be mounted at least partially within said U-shaped wall of said first section, said U-shaped wall and said dome-shaped member being sized and shaped so as to define a trough therebetween for receiving an impression-taking material therein, said second section being movable relative to said first section in said first direction, said dome-shaped member having first and second movable members, each of which is movable in a second direction substantially perpendicular to said longitudinal axis in response to the movement of said second section in said first direction.

13. The dental tray of claim 12, wherein said first section has a ramp, a first lateral side and a second lateral side opposite said first lateral side; and wherein said first and second movable members of said dome-shaped member are sized and shaped so as to engage said ramp in response to the movement of said second section in said first direction so as to cause said first and second movable members to move in said second direction toward said first and second lateral sides, respectively, of said first section.

14. The dental tray of claim 13, wherein said ramp includes a first wall portion, which is located adjacent said first lateral side of said first section, and a second wall portion, which is located adjacent said second lateral side of said first section; and wherein said first and second movable members have first and second guides, respectively, depending therefrom, said first and second guides being configured to engage said first and second wall portions, respectively, in response to the movement of said second section in said first direction so as to cause said first and second movable members to move in said second direction toward said first and second lateral sides, respectively, of said first section.

15. The dental tray of claim 14, wherein said second section has first and second hinges pivotally connecting said first and second movable members, respectively, to a handle portion of said second section.

16. The dental tray of claim 14, wherein said first and second movable members are positioned adjacent to each other such that they cooperate to define a substantially hollow space in said dome-shaped member, said ramp being positioned in said space, and wherein each of said first and second movable members has a cutout adjacent a top portion thereof such that an overflow of the impression material can be received in said space from said trough through said cutouts.

17. A method for taking an impression of a person's teeth with the use of a dental tray having a first section and a second section, the first section having a longitudinal axis and a generally U-shaped outer wall, the second section having a dome-shaped inner member mounted at least partially within the U-shaped wall of the first section so as to define a trough therebetween, the second section being movable relative to the first section in a first direction substantially parallel to the longitudinal axis of the first section, the dome-shaped member having first and second movable members, each of which is movable in a second direction substantially perpendicular to the longitudinal axis in response to the movement of the second section in the first direction, said method comprising the steps of: placing an impression-taking material in the trough of the tray; inserting the tray into a mouth of the person; moving the tray such that the teeth are inserted into the impression material placed in the trough; and moving the second section in the first direction so as to cause the first and second movable members to move in the second direction.

18. The method of claim 17, wherein the first section of the tray has a first lateral side and a second lateral side opposite the first lateral side; and wherein the first and second movable members are movable in the second direction toward the first and second lateral sides, respectively, of the first section in response to the movement of the second section in the first direction.

19. The method of claim 17, wherein the first section includes a ramp; and wherein the first and second movable members of the second section are sized and shaped so as to engage the ramp in response to the movement of the second section in the first direction so as to cause the first and second movable members to move in the second direction toward the first and second lateral sides, respectively, of the first section.

20. The dental tray of claim 19, wherein the ramp includes a first wall portion, which is located adjacent the first lateral side of the first section, and a second wall portion, which is located adjacent the second lateral side of the first section; and wherein the first and second movable members have first and second guides, respectively, depending therefrom, the first and second guides being configured to engage the first and second wall portions, respectively, in response to the movement of the second section in the first direction so as to cause the first and second movable members to move in the second direction toward the first and second lateral sides, respectively, of the first section, the first and second movable members being positioned adjacent to each other such that they cooperate to define a substantially hollow space in the dome-shaped member, the ramp being positioned in the space.

* * * * *